(12) United States Patent
Hamilton

(10) Patent No.: US 6,413,083 B1
(45) Date of Patent: Jul. 2, 2002

(54) COMPUTERIZED SYSTEM AND METHOD FOR CORRECTING TOOTH-SIZE DISCREPANCIES

(75) Inventor: David C. Hamilton, New Castle, PA (US)

(73) Assignee: Dentsply Research & Development Corp.

( * ) Notice: Subject to any disclaimer, the term of this patent is extended or adjusted under 35 U.S.C. 154(b) by 0 days.

(21) Appl. No.: 09/436,588

(22) Filed: Nov. 9, 1999

(51) Int. Cl.[7] .................................................. A61C 3/00
(52) U.S. Cl. .......................................... 433/24; 433/72
(58) Field of Search ................................ 433/24, 8, 20, 433/72

(56) References Cited

U.S. PATENT DOCUMENTS 5,447,432 A * 9/1995 Andreiko et al. .............. 433/24
5,683,243 A * 11/1997 Andreiko et al. .............. 433/24

OTHER PUBLICATIONS

Bolton, Wayne A., "The Clinical Application of a Tooth–Size Analysis," American Journal of Orthodontics, vol. 48, No. 7, pp. 504–529, Jul. 1962.

Bolton, Wayne A., "Disharmony in Tooth Size and Its Relation to the Analysis and Treatment of Malocclusion," angle Orthodontist, vol. 28, pp. 113, 130, 1958.

Hamilton, David C., Basic Code for Performing Bolton Anaylsis on a Sharp Hand Held Calculator, 1979.

* cited by examiner

Primary Examiner—Nicholas D. Lucchesi
(74) Attorney, Agent, or Firm—James B. Bieber; Douglas R. Hura

(57) ABSTRACT

A computerized system and method for diagnosing a tooth-size discrepancy and recommending an ideal arch size based on the size of an individual patient's teeth. The computerized system includes a central processing unit, a first storage device, a second storage device, a dynamic memory device, and input/output devices. The input devices include a computerized caliper for measuring the mesiodistal width of teeth and directly inputting the measurements into the computerized system. The computerized system and method determine the existence of a tooth-size discrepancy, the necessary anatomical correction, at least one tooth responsible for the tooth-size discrepancy, and a recommended arch wire size.

37 Claims, 6 Drawing Sheets

COMPUTERIZED SYSTEM AND METHOD FOR CORRECTING TOOTH-SIZE DISCREPANCIES

FIELD OF THE INVENTION

The present invention relates to the field of orthodontics, in particular a computerized system and method for identifying and correcting tooth-size discrepancies, and determining a recommended arch size predicated on a patient's cranial-facial morphology and tooth size.

BACKGROUND INFORMATION

In the field of orthodontics, a mathematical ratio exists between the size (mesiodistal width) of the upper (maxillary) and lower (mandibular) teeth. This mathematical ratio should exist in an ideal dental occlusion. More often than not, and particularly in patients with orthodontic problems, a tooth-size discrepancy exists. Although there are no reliable epidemiological studies confirming these statistics, it is estimated that approximately one-third of the American public have tooth sizes that are proportional and within a reasonable range of an ideal occlusion. The remaining two-thirds of the American public, however, have teeth where the mathematical ratio is not ideal and there exists a modest to severe tooth-size discrepancy or incompatibility.

In a scientific research paper entitled "Disharmony in Tooth Size and Its Relation to the Analysis and Treatment of Malocclusion" by Dr. Wayne A. Bolton, a method is described for identifying the presence and magnitude of a tooth-size discrepancy (the "Bolton Analysis"). This method may be performed on the six anterior teeth (two canines, two laterals, and two central incisors) or on twelve teeth (the six anterior teeth, the four premolar teeth, and the two first molar teeth). The mathematical ratio is compared to the ideal mathematical ratio, which is 0.772 for the six anterior teeth, and 0.913 for the twelve teeth analysis. This comparison identifies any existing tooth-size discrepancy and the magnitude of the tooth-size discrepancy, which is the difference between the mathematical ratio and the ideal mathematical ratio.

Typically, the Bolton Analysis is performed using the tables provided in Bolton's paper, a slide rule, which is no longer manufactured, or a calculator. Therefore, determining the existence of a tooth-size discrepancy using the Bolton Analysis can be very tedious and time consuming. While the Bolton Analysis determines the existence and the magnitude of a tooth-size discrepancy, it does not quantify the mathematical correction necessary in the maxillary and/or mandibular teeth to achieve an ideal occlusion. Thus, there exists a need for a computerized system that measures teeth and accurately determines the existence and magnitude of a tooth-size discrepancy in an easy and expeditious manner.

The failure of an orthodontist to recognize the existence and amount of the tooth-size discrepancy during diagnosis, and to attain a close to ideal ratio of tooth structure during treatment, may result in treatment problems, such as crowding or spacing of the maxillary and/or mandibular teeth. Deviations from the ideal ratio may also result in a relapse of treatment and/or functional, aesthetic and health problems.

A problem arises, however, when the orthodontist attempts to correct the tooth-size discrepancy determined using the Bolton Analysis. Since the results of the Bolton Analysis are directly related to a ratio, the results do not accurately address the amount of actual anatomical correction necessary in either the maxillary or mandibular arch. As soon as a change is undertaken in any direction, the ratio changes. An orthodontist assuming that a tooth-size discrepancy can be corrected merely by adding to or removing the amount of tooth structure indicated by the results of the Bolton Analysis, in either the maxillary or mandibular arch, will err. Moreover, the results of the Bolton Analysis do not clearly demonstrate to the orthodontist or researcher the actual tooth or teeth prompting the tooth-size discrepancy. Thus, there exists a further need for a computerized system that determines the amount of anatomical correction necessary using the results of the Bolton Analysis. It would be desirable if this system would illustrate, on a monitor and/or in a printer output, the actual and average size of each tooth so that it is immediately apparent to the doctor the tooth or teeth that may be responsible for the tooth-size discrepancy.

Preformed arch wires such as super-elastic preformed arch wires are frequently used during the first and second phases of treatment to level, align, torque, and/or shape the teeth and the arches. Current orthodontic use of preformed arch wires (one for the maxillary arch, one for the mandibular arch) means that approximately 17% of patients are treated with an arch wire that is too large and 17% of patients are treated with an arch wire that is too small. Since these preformed arch wires are not adjustable to the patient's facial size, they may create problems by over expansion or constriction of the maxillary and/or mandibular arch. These problems might be corrected later in treatment, when it is least desired, and would extend the treatment time. In addition, the use of these preformed wires may also result in "round tripping," i.e., moving the teeth in the wrong direction and then having to recorrect the teeth. Thus, there exists a further need for a computerized system that determines the ideal arch wire size to effectuate a more precise and stable treatment.

SUMMARY OF THE INVENTION

The computerized system according to an example embodiment of the present invention determines the existence and magnitude of a tooth-size discrepancy, the necessary anatomical correction, the identity of the individual tooth or teeth responsible for the tooth-size discrepancy and the recommended arch wire size to effectuate treatment of the tooth-size discrepancy. The computerized system includes a computer with various input/output devices that include a computerized caliper. The computer executes a program that performs an analysis and outputs (1) the sums of the maxillary and mandibular arches, (2) the necessary anatomical correction, (3) the individual tooth or teeth responsible for the tooth-size discrepancy and (4) the recommended arch wire size. The computerized caliper is used to measure the mesiodistal width of each tooth. The computerized caliper directly inputs each tooth-size measurement into the computer.

Once the user has inputted the individual measurements for the teeth involved in the analysis, the user may compare the measurements with the average measurement for each tooth via a monitor and/or a printer output.

Using the inputted information, the program determines the magnitude of the tooth size discrepancy, the necessary anatomical correction and the recommended arch wire size. Once the tooth-size discrepancy is determined, the user may utilize the necessary anatomical correction along with a comparison of the measurements to the average sizes to determine the proper diagnosis, i.e., how much correction to make in the maxillary teeth, the mandibular teeth or a combination of the two.

The method according to the example embodiment of the present invention uses the selected arch wires during the entire course of treatment. The arch wires are selected on the basis of the tooth-size measurements of the patient.

In other embodiments, the constants used to calculate the tooth-size discrepancy, anatomical correction necessary, and the arch wire size are adjusted for the statistical differences based on race.

BRIEF DESCRIPTION OF THE DRAWINGS

FIG. 2A illustrates a first screen display of a program according to the present invention.

FIG. 2B illustrates a second screen display of a pull down menu from the screen display shown in FIG. 2A.

FIG. 2C illustrates a third screen display of a program implementing the flow chart shown in FIG. 3.

DETAILED DESCRIPTION

Figure 1:
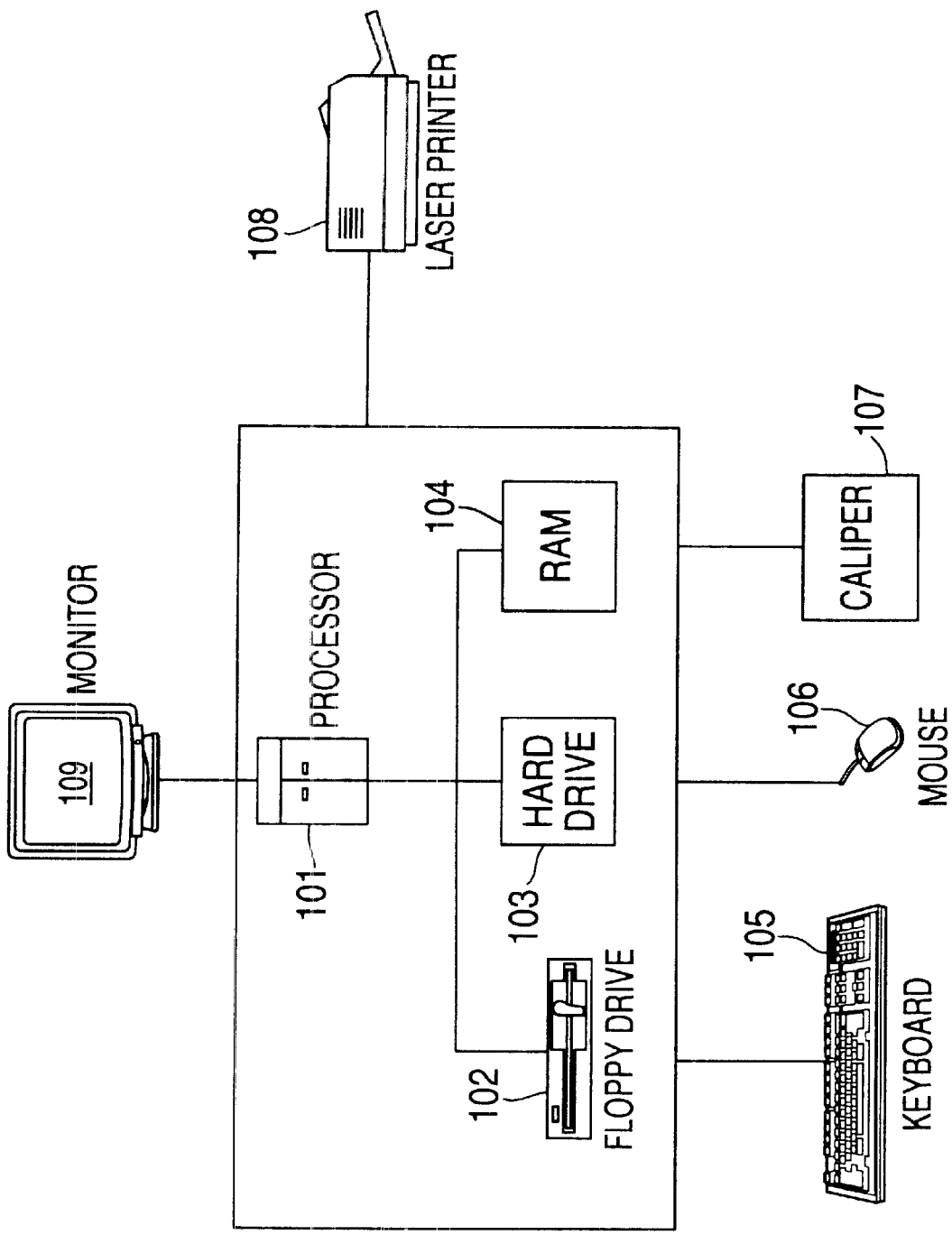
FIG. 1 illustrates a computer system according to the present invention.

An example embodiment of the present invention is explained in further detail with reference to the drawings. FIG. 1 illustrates a computer system according to the present invention. The computer system includes a central processing unit 101, a first storage device 102, a second storage device 103, a dynamic memory device 104, and input/output devices 105, 106, 107, 108 and 109. The central processing unit 101 is for executing computer programs, in particular a software program determining tooth-size discrepancy, necessary anatomical correction, the tooth or teeth responsible for the tooth-size discrepancy, and arch wire size, and for managing and controlling the operation of the computer system.

The first storage device 102, such as a floppy disk drive, is coupled to the central processing unit 101 for reading and writing data and computer programs to and from removable storage media, such as floppy disks. The second storage device 103 is also coupled to the central processing unit 102 and provides a means for storing computer programs and data. The second storage device 103, however, may be, for example, a hard disk drive having a high storage capacity.

The dynamic memory device 104, for example a RAM, is coupled to the central processing unit 101. The computer system includes typical input/output devices, such as, for example, a keyboard 105, a mouse 106, a printer 108, and a monitor 109. The computer also includes an input/output device for measuring the mesiodistal width of teeth, such as, for example a computerized caliper 107.

In the example embodiment the computerized caliper 107 may be a digital caliper such as, for example, the Fowler "Max-Cal: The Computerized Caliper," order no. 54-200-000 or 54-200-0008. This device may be modified in accordance with the example embodiment. For example, the measuring tines may be retooled so that they are sharply pointed and appropriate for highly accurate measurement of individual teeth. The actual teeth or a plaster model of the teeth may be measured. It should be noted that if the actual teeth are measured, then the computerized caliper should be sterilized.

A driver is provided to read the input from the caliper 107. This driver is capable of detecting each measurement taken by the caliper 107 after an enter button of the caliper 107 has been pressed. The driver, for example, determines which communications port of the computer system shown in FIG. 1 the caliper is connected. Further, the driver, for example, establishes a communications link between the caliper 107 and the computer system.

Figures 2A, 2B:
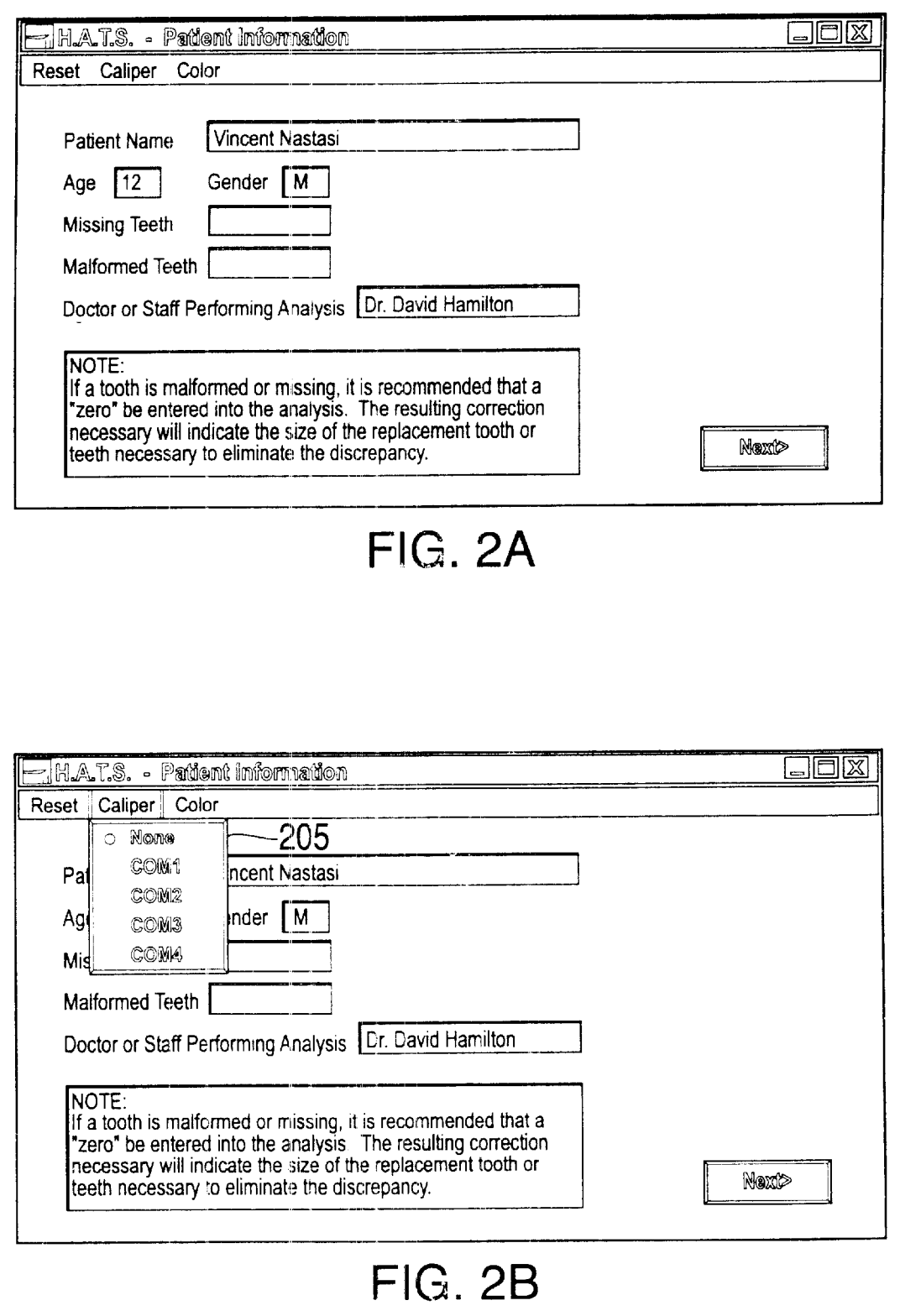

FIG. 2A illustrates a screen display in which the user enters patient information, for example, the patient's name, age and gender and any missing or malformed teeth.

FIG. 2B illustrates a pull-down menu 205 for selecting whether the keyboard 105 or the caliper 107 will be used to input the measurements. If the measurements will be entered via the keyboard 105, the user should select none. If the measurements will be entered via the caliper 107, the user should select the communication port, i.e. COM1, COM2, etc., to which the caliper 107 is connected. Once the user has selected the input device and inputted the patient information, the user must select the "NEXT" button to implement the program shown in FIG. 3.

Figure 2C:
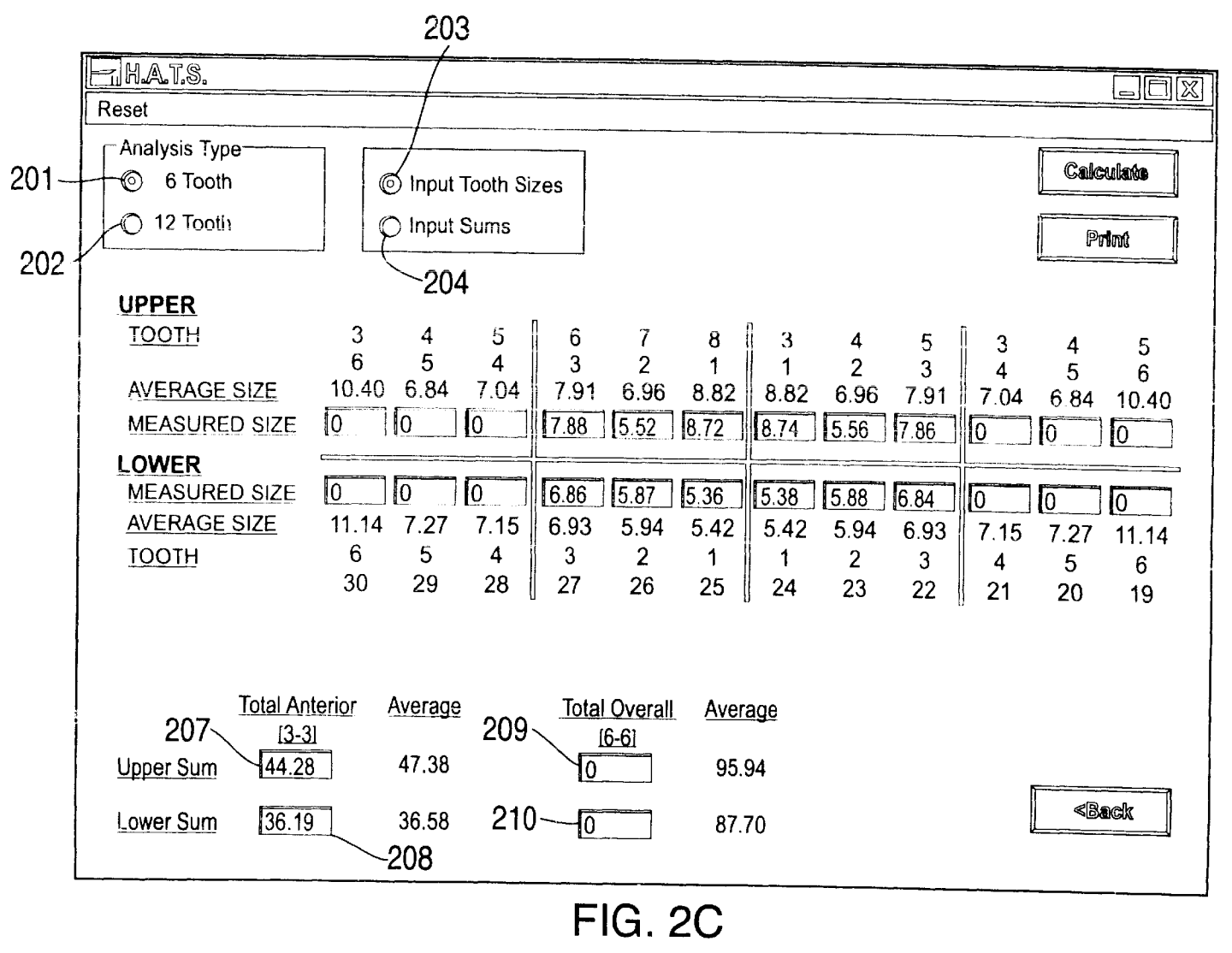
Figure 2D:
FIG. 2D illustrates a fourth screen display of a program implementing the flow chart shown in FIG. 3.
Figure 3:
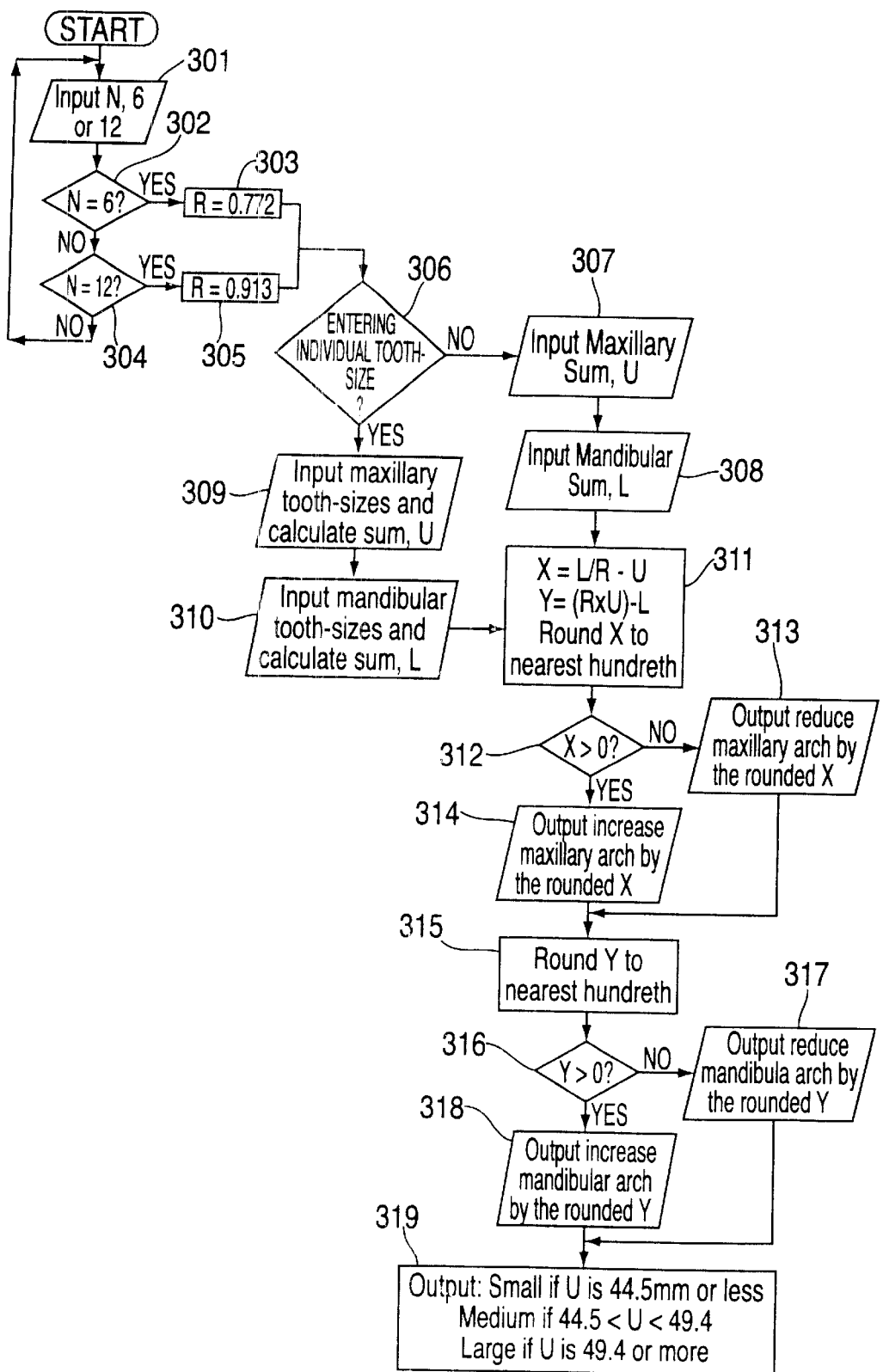
FIG. 3 illustrates a flowchart of a software program according to the present invention for determining tooth-size discrepancy, necessary anatomical correction, individual teeth responsible for the tooth-size discrepancy and a recommended arch wire size for the maxillary and mandibular arches.

FIGS. 2C and 2D are screen displays of a program implementing the flow chart shown in FIG. 3. The program may be implemented using any conventional programming language, such as C++.

FIG. 2C illustrates a screen display in which the user has inputted the individual tooth sizes necessary for a six-tooth analysis. As shown in FIG. 2C, the user may select six-tooth analysis at radio button 201 or twelve-tooth analysis at radio button 202. The user may also select to input either the individual tooth sizes at radio button 203 or the sums of the maxillary and mandibular arches at radio button 204. In this case, the user has selected six-tooth analysis and to input the individual tooth sizes. These selections may be accomplished via the keyboard 105 or the mouse 107. If the user had selected to input the sums rather than the individual measurements, then the user inputs the sums at entry points 207 and 208 for six-tooth analysis and entry points 209 and 210 for twelve-teeth analysis.

At this stage, the user inputs the measurements via the keyboard 105 or the caliper 107. If the user has selected the keyboard 105 as the input device, the user enters the measurements in the order indicated using the keyboard 105 and press the enter key of the keyboard 105. In the example embodiment, the order for entering the measurements is indicated by highlighting the measurement to be taken as shown at entry point 206. Above entry point 26, the average size for the upper right canine, 7.91 mm, is shown.

If the user has selected the caliper 107 as the input device, the user uses the caliper 107 to measure the mesiodistal width of each of the teeth and presses the enter button on the caliper 107 after each measurement. After all the measurements are entered the user should click on the "print" button 211 and/or "calculate" button 212. The "print" button 211 prints out the screen display as shown in FIG. 2C with all of the inputted measurements. The "calculate" button 212 executes the determination of the arch size, tooth-size discrepancy, necessary correction, and the arch wire size, resulting in a screen display as shown, for example, in FIG. 2D.

FIG. 2D illustrates a screen display of an analysis summary of an output of a program implementing the flow chart shown in FIG. 2. The screen display shows the maxillary arch sum 213, mandibular arch sum 214, any necessary anatomical correction 215, 216, and the recommended arch wire size 217. In this particular case, the sum of the maxillary arch is 44.28 mm and the sum of the mandibular arch is 36.19 mm. The necessary anatomical correction is an increase in the maxillary arch by 2.6 mm or a reduction of the mandibular arch by 2.01 mm. This indicates that the mesiodistal width of the maxillary teeth should be increased by 2.6 mm, and the mesiodistal width of the mandibular teeth should be decreased by 2.01 mm. The orthodontist, however, may also decide to implement a treatment that is a combination of the two calculations. The recommended arch wire size 217, in this case, is "small."

The teeth responsible for the tooth-size discrepancy may be determined by viewing the screen display shown in FIG. 2C after inputting all of the individual teeth measurements. This particular screen display shows the average size for each tooth either above or below the tooth's measurement. For the maxillary teeth, the average size is displayed above each measurement. The average size for the mandibular teeth is displayed below each measurement. The user may determine the teeth responsible for the tooth-size discrepancy by comparing the measurement to the average size for each particular tooth.

FIG. 3 illustrates a flowchart of a software program determining tooth-size discrepancy, the necessary tooth-size correction, the individual teeth responsible for the tooth-size discrepancy, and arch wire size according to the present invention.

During execution of the program, a user selects either six or twelve via the keyboard 105 or the mouse 106 to indicate whether six-tooth analysis or twelve tooth analysis will be used (Block 301). Next, the program determines whether six-tooth or twelve tooth analysis was selected (Blocks 302 and 304). If the user indicated six-tooth analysis, the ideal mathematical ratio R is set to 0.772 (Block 303). If the user indicated twelve-tooth analysis, the ideal mathematical ratio is set to 0.913 (Block 305), otherwise the program returns to the beginning of the program (Block 301).

After the ideal mathematical ratio R is set, the program determines whether individual tooth sizes or the sums of the individual tooth sizes of each arch will be entered (Block 306). If the sums are to be entered, the user inputs the sum of the mesiodistal widths of the maxillary teeth U (Block 307). Likewise, the user inputs the sum of the mesiodistal widths of the mandibular teeth L (Block 308). If the mesiodistal widths for the individual teeth are to be inputted, the user is prompted to input the individual mesiodistal widths for the maxillary teeth and the sum of the mesiodistal widths of the maxillary teeth U is determined (Block 309). Likewise, the user is prompted to input the individual mesiodistal widths for the mandibular teeth and the sum of the mesiodistal widths of the mandibular teeth L is determined (Block 310).

Next, the necessary anatomical correction in the maxillary and mandibular arches are determined. The magnitude of the necessary anatomical correction in the maxillary arch, X, is rounded to the nearest hundredth of millimeters (Block 311).

The necessary anatomical correction for the maxillary arch, X, is determined according to the following equation:

$$X = L/R - U \quad (1)$$

The necessary anatomical correction for the mandibular arch, Y, is determined according to the following equation:

$$Y = (U \times R) - L \quad (2)$$

Then, the necessary anatomical correction for the maxillary arch, X, is compared to zero (Block 312). If the necessary anatomical correction for the maxillary arch, X, is greater than zero, then the program outputs that the mesiodistal width of the teeth in the maxillary arch should be reduced by the rounded X (Block 313). If the necessary anatomical correction for the maxillary arch, X, is less than zero, then the program outputs that the mesiodistal width of the teeth in the maxillary arch should be increased by the rounded X (Block 314). If the necessary anatomical correction for the maxillary arch equals zero, then there is no tooth-size discrepancy and no anatomical correction is necessary.

Next, the magnitude of the necessary anatomical correction in the mandibular arch, Y, is rounded to the nearest hundredth of millimeters (Block 315).

The necessary anatomical correction in the mandibular arch, Y, is then compared to zero (Block 316). If the necessary anatomical correction, Y, is greater than zero, then the program outputs that the mesiodistal width of the teeth in the mandibular arch should be reduced by the rounded Y (Block 317). If the necessary anatomical correction, Y, is less than zero (0), then the program outputs that the mesiodistal width of the teeth in the mandibular arch should be increased by the rounded Y for the mandibular arch (Block 318). If the necessary anatomical correction, Y, for the mandibular arch equals zero, then there is no tooth-size discrepancy and no anatomical correction is necessary.

Finally, the recommended arch wire size is selected and displayed to the user (Block 319). If the sum of the maxillary teeth is less than 44.5 mm, then a set of small arch wires is selected for the maxillary and mandibular arches. If the sum of the maxillary teeth is greater than 44.5 mm but less than 49.4 mm, then a set of medium arch wires is selected for the maxillary and mandibular arches. If the sum of the maxillary teeth is greater than 49.4 mm, then a set of large arch wires is selected for the maxillary and mandibular arches. These parameters were determined based on the standard deviation of the average sum of the maxillary anterior tooth sizes of the patients with an untreated ideal occlusion used in the Bolton scientific study.

Once the necessary anatomical correction in the maxillary and mandibular arches has been calculated according to the present invention, the orthodontist may select a conventional method of treatment. The orthodontist may correct the arch size discrepancy by one or a combination of the following methods:

1. Selective and measured reduction of the mesiodistal widths of selected teeth by interproximal stripping (reduction of the enamel surfaces by the necessary correction).
2. Extraction.
3. Prosthetic replacement of teeth or addition of teeth in accordance with the necessary correction.
4. Prosthetic treatment utilizing composite additions, veneers or jacket crowns altering the size of existing teeth.

The recommended arch wires should be used during the entire course of treatment. In the example embodiment, the selected arch wires are used through the entire course of treatment, i.e., from beginning through the end. Use of an arch wire according to the present invention, addresses three problems. First, determination of the arch size by measurement of the teeth assures, with few exceptions, that the treatment outcome will provide facial and skeletal, functional and aesthetic harmony with the patient's face and jaws. Second, the arch wire selected by the present invention is adapted to the individual patient's tooth-size preventing over-expansion or constriction of the arch during the course of treatment. Third, the arch wire according to the present invention may prevent "round tripping" caused by moving teeth in wrong directions and then correcting them again. Such movement may create severe iatrogenic sequelae.

Figure 4:
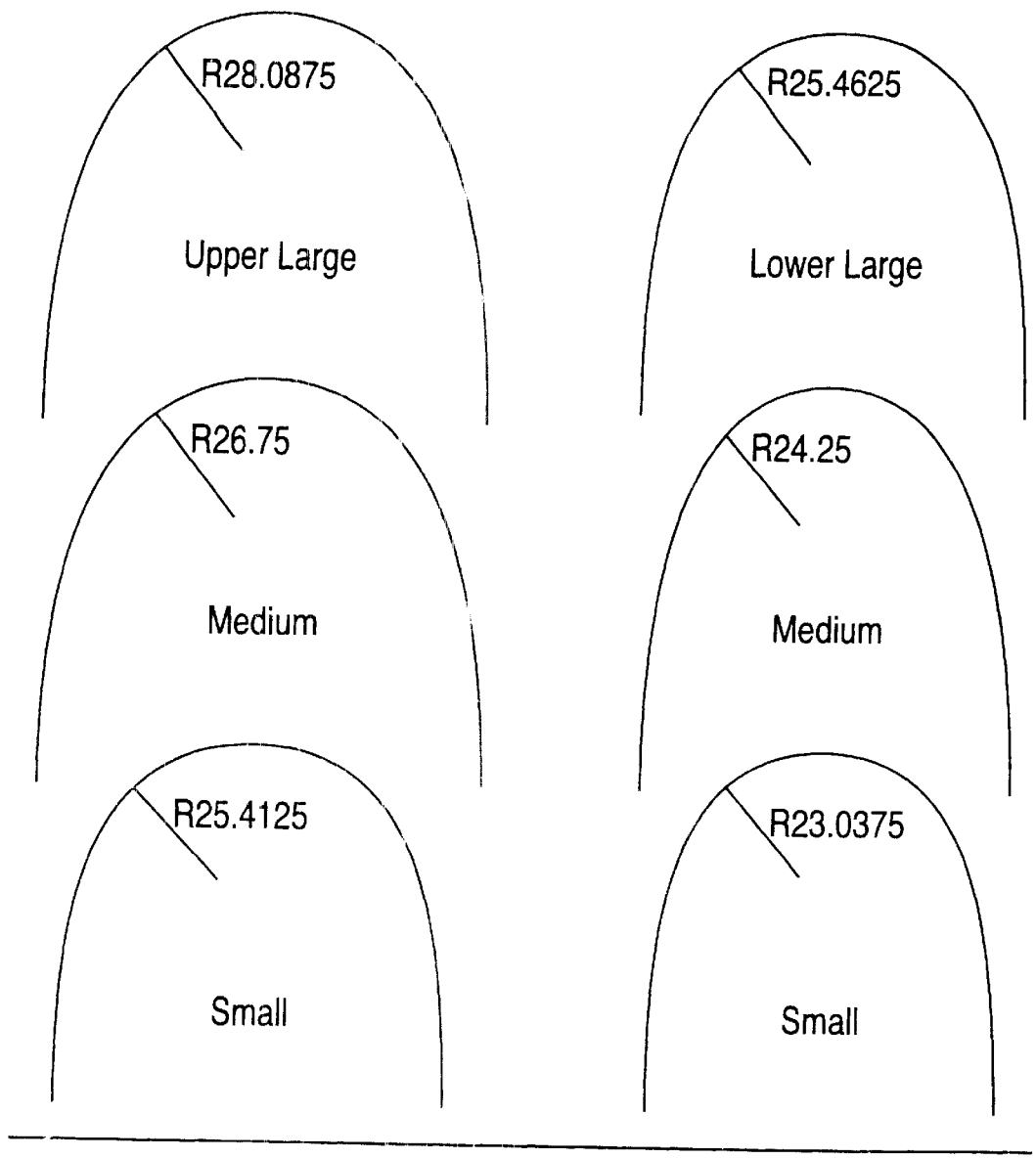
FIG. 4 illustrates a view of a set of small medium and large arch wires according to the present invention.

FIG. 4 is an illustration of a set of small, medium and large arch wires according to the present invention. Each set contains an arch wire for the maxillary arch and the mandibular arch. The large arch wire for the maxillary arch has an approximate radius of curvature of 28.0875 mm. The large arch wire for the mandibular arch has a radius of curvature approximately equal to 25.4625 mm. The medium arch wire for the maxillary arch has a radius of curvature of approximately 26.75 mm. The medium arch wire for the mandibular arch has a radius of curvature of approximately 24.25 mm. The small arch wire for the maxillary teeth has a radius of curvature of approximately 25.4125 mm. The radius of curvature is approximately 23.0375 mm for the small arch wire for the mandibular arch. The radius of curvatures for each of the arch wires is determined from historical patient data, with the small and large arch wires being plus and minus one standard deviation.

The arch wires are made of, for example, stainless steel and/or nickel-titanium (NiTi) and may be, for example, either round, rectangular or square. The size for round arch wires made of NiTi are, for example, 0.014 inch, 0.016 inch, and 0.018 inch. The dimensions for rectangular NiTi arch wire are, for example, 0.016 inch×0.016 inch, 0.016 inch×0.022 inch, 0.017 inch×0.025 inch, 0.018 inch×0.025 inch, 0.02 inch×0.02 inch, and 0.021 inch×0.028 inch. The dimensions for Bioforce arch wires are, for example, 0.016 inch×0.016 inch, 0.016 inch×0.022 inch, 0.018 inch×0.018 inch, 0.018 inch×0.025 inch, 0.02 inch×0.02 inch, 0.021 inch×0.028 inch.

The tooth-size discrepancy, necessary correction, and arch wire size are determined using, in part, the ideal mathematical ratio from the Bolton Analysis. The original Bolton Analysis as described in the paper entitled "Disharmony in Tooth Size and Its Relation to the Analysis and Treatment of Malocclusion" included only Caucasian patients. In another embodiment, the present invention adjusts its calculations to compensate for the modest but statistically significant difference specific to other races. The method and process remain the same, however, the ideal ratio and average sizes for individual teeth would vary based on these statistical differences.

What is claimed is:

1. A system for selecting at least one arch wire, comprising:
    an input device inputting at least one of:
        i) at least one sum of a plurality of tooth sizes, and
        ii) a plurality of tooth sizes,
    a processor, the input device being interfaced to the processor and the processor receiving from the input device the at least one of
        i) the at least one sum, and
        ii) the plurality of tooth sizes,
if the processor receives the plurality of tooth sizes from the input device, the processor determines the at least one sum as a function of the plurality of tooth sizes, the processor selecting at least one arch wire as a function of the at least one sum; and
    a display device displaying the selected at least one arch wire.

2. The system according to claim 1, wherein the input device is a digital caliper.

3. The system according to claim 2, wherein the at least one sum includes a sum of tooth sizes of a maxillary arch and a sum of tooth sizes of a mandibular arch, the processor determines at least one of an anatomical correction in the maxillary arch and an anatomical correction in the mandibular arch as a function of the sum of tooth sizes of the maxillary arch and the sum of tooth sizes of the mandibular arch, and the display device displays the at least one of the anatomical correction in the maxillary arch and the anatomical correction in the mandibular arch.

4. The system according to claim 3, wherein the processor determines the anatomical correction in the maxillary arch using the following formula:

$$X = L/R - U,$$

wherein,
    X is the anatomical correction in the maxillary arch,
    L is the sum of the tooth sizes of the mandibular arch,
    R is a ratio, and
    U is the sum of the tooth sizes of the maxillary arch.

5. The system according to claim 4, wherein the ratio is one of 0.772 for a six-tooth analysis and 0.913 for a twelve-tooth analysis.

6. The system according to claim 3, wherein the processor determines the anatomical correction in the mandibular arch using the following formula:

$$Y = (U \times R) - L,$$

wherein,
    Y is the anatomical correction in the mandibular arch,
    U is the sum of the tooth sizes of the maxillary arch,
    R is a ratio, and
    L is the sum of the tooth sizes of the mandibular arch.

7. The system according to claim 6, wherein the ratio is one of 0.772 for a six-tooth analysis and 0.913 for twelve-tooth analysis.

8. The system according to claim 1, wherein at least one sum includes a sum of tooth sizes of a maxillary arch and a sum of tooth sizes of a mandibular arch, and wherein the selected at least one arch wire includes an arch wire for the maxillary arch and an arch wire for the mandibular arch.

9. The system according to claim 8, wherein if the sum of tooth sizes of the maxillary arch is less than or equal to 44.5 mm, the arch wire selected for the maxillary arch has a radius of curvature of approximately 25.4125 mm and the arch wire selected for the mandibular arch has a radius of curvature of approximately 23.0375 mm.

10. The system according to claim 8, wherein if the sum of tooth sizes of the maxillary arch is between 44.5 mm and 49.4 mm, the arch wire selected for the maxillary arch has a radius of curvature of approximately 26.75 mm and the arch wire selected for the mandibular arch has a radius of curvature of approximately 24.25 mm.

11. The system according to claim 8, wherein if the sum of tooth sizes of the maxillary arch is at least 48.4 mm, the arch wire selected for the maxillary arch has a radius of curvature of approximately 28.0875 mm and the arch wire selected for the mandibular arch has a radius of curvature of 25.4625 mm.

12. The system according to claim 1, wherein the input device is a keyboard.

13. A system for determining an anatomical correction for at least one of a maxillary arch and a mandibular arch, comprising:
　a caliper for measuring at least one tooth size;
　a processor, the caliper being interfaced to the processor, the processor receiving from the caliper the at least one tooth size, the processor determining at least one sum of a plurality of tooth sizes as a function of the least one tooth size, the processor determining the anatomical correction for the at least one of the maxillary arch and the mandibular arch as a function of the least one sum; and
　a display device displaying the determined anatomical correction.

14. The system according to claim 13, wherein the at least one sum includes a sum of tooth sizes of the maxillary arch and a sum of tooth sizes of the mandibular arch, the processor determining the anatomical correction for the at least one of the maxillary arch and the mandibular arch as a function of the sum of tooth sizes of the maxillary arch and the sum of tooth sizes of the mandibular arch.

15. The system according to claim 13, wherein the processor determines the anatomical correction in the maxillary arch using the following formula:

$$X = L/R - U,$$

wherein,
　X is the anatomical correction in the maxillary arch,
　L is the sum of the tooth sizes of the mandibular arch,
　R in the ratio, and
　U in the sum of the tooth sizes of the maxillary arch.

16. The system according to claim 15, wherein the ratio is one of 0.772 for a six-tooth analysis and 0.913 for a twelve-tooth analysis.

17. The system according to claim 13, wherein the processor determines the anatomical correction in the mandibular arch using the following formula:

$$Y = (U \times R) - L,$$

wherein,
　Y is the anatomical correction in the mandibular arch,
　U is the sum of the tooth sizes of the maxillary arch,
　R is a ratio, and
　L is the sum of the tooth sizes of the mandibular arch.

18. The system according to claim 17, wherein the ratio is one of 0.772 for a six-tooth analysis and 0.913 for a twelve-tooth analysis.

19. A computerized method for selecting at least one arch wire, comprising the steps of:
　receiving from an input device by a processor at least one of:
　　i) at least one sum of a plurality of tooth sizes, and
　　ii) a plurality of tooth sizes;
　if the plurality of tooth sizes are received, determining by the processor the at least one sum; and
　selecting by the processor the at least one arch wire as a function of the at least one sum.

20. The computerized method according to claim 19 further comprising the step of:
　displaying the selected at least one arch wire.

21. The computerized system according to claim 19, wherein the input device is a digital caliper.

22. The computerized method according to claim 19, wherein the at least one sum includes a sum of tooth sizes of a maxillary arch and sum of tooth sizes of a mandibular arch, further comprising the steps of:
　determining by the processor at least one of an anatomical correction in the maxillary arch and an anatomical correction in the mandibular arch as a function of the sum of tooth sizes of the maxillary arch and the sum of tooth sizes of the mandibular arch; and
　displaying the at least one of the anatomical correction in the maxillary arch and the anatomical correction in the mandibular arch.

23. The computerized method according to claim 22, wherein the step of determining the at least one of the anatomical correction in the maxillary arch and the anatomical correction in the mandibular arch includes a step of determining the anatomical correction in the maxillary arch using the following formula:

$$X = L/R - U,$$

wherein,
　X is the anatomical correction in the maxillary arch,
　L is the sum of the tooth sizes of the mandibular arch,
　R is a ratio, and
　U is the sum of the tooth sizes of the maxillary arch.

24. The computerized method according to claim 23, wherein the ratio is one of 0.772 for a six-tooth analysis and 0.913 for a twelve-tooth analysis.

25. The computerized method according to claim 22, wherein the step of determining the at least one of the anatomical correction in the maxillary arch and the anatomical correction in the mandibular arch includes a step of determining the anatomical correction in the mandibular arch using the following formula:

$$Y = (U \times R) - L,$$

wherein,
　Y is the anatomical correction in the mandibular arch,
　U is the sum of the tooth sizes of the maxillary arch,
　R is a ratio, and
　L is the sum of the tooth sizes of the mandibular arch.

26. The computerized method according to claim 25, wherein the ratio is one of 0.772 for a six-tooth analysis and 0.913 for a twelve-tooth analysis.

27. The computerized method according to claim 19, wherein the at least one sum includes a sum of tooth sizes in a maxillary arch and a sum of tooth sizes in a mandibular arch, wherein the selecting step includes a step of:
　if the sum of the tooth sizes in the maxillary arch is less than or equal to 44.5 mm, selecting an arch wire for the maxillary arch having a radius of curvature of approximately 25.4125 mm and selecting an arch wire for the mandibular arch having a radius of curvature of approximately 23.0375 mm.

28. The computerized method according to claim 19, wherein the at least one sum includes a sum of tooth sizes in a maxillary arch and a sum of tooth sizes in a mandibular arch, wherein the selecting step includes a step of:
　if the sum of tooth sizes of the maxillary arch is between 44.5 mm and 49.4 mm, selecting an arch wire for the maxillary arch having a radius of curvature of approximately 26.75 mm and selecting an arch wire for the mandibular arch having a radius of curvature of approximately 24.25 mm.

29. The computerized method according to claim 19, wherein the at least one sum includes a sum of tooth sizes in a maxillary arch and a sum of tooth sizes in a mandibular arch, wherein the selecting step includes a step of:

if the sum of tooth sizes of the maxillary arch is at least 48.4 mm, selecting an arch wire for the maxillary arch having a radius of curvature of approximately 28.0875 mm and selecting an arch wire for the mandibular arch having a radius of curvature of 25.4625 mm.

30. The system according to claim 19, wherein the input device is a keyboard.

31. A computerized method for determining an anatomical correction for at least one of a maxillary arch and a mandibular arch, comprising the steps of:

measuring with a caliper a plurality of tooth sizes;

receiving by the processor from the caliper the plurality of tooth sizes;

determining by the processor the at least one sum as a function of the plurality of tooth sizes; and determining the anatomical correction for the at least one of the maxillary arch and the mandibular arch as a function of the at least one sum; and displaying the determined anatomical correction.

32. The computerized method according to claim 31, wherein the at least one sum includes a sum of tooth sizes of a maxillary arch and sum of tooth sizes of a mandibular arch.

33. The computerized method according to claim 32, wherein the determining step includes a step of:

determining the anatomical correction in the maxillary arch using the following formula:

$$X = L/R - U,$$

wherein,

X is the anatomical correction in the maxillary arch,

L is the sum of the tooth sizes of the mandibular arch,

R is a ratio, and

U is the sum of the tooth sizes of the maxillary arch.

34. The computerized method according to claim 33, wherein the ratio is one of 0.772 for a six-tooth analysis and 0.913 for a twelve-tooth analysis.

35. The computerized method according to claim 32, wherein the determining step includes a step of determining the anatomical correction in the mandibular arch using the following formula:

$$Y = (U \times R) - L,$$

wherein,

Y is the anatomical correction in the mandibular arch,

U is the sum of the tooth sizes of the maxillary arch,

R is a ratio, and

L is the sum of the tooth sizes of the mandibular arch.

36. The computerized method according to claim 35, wherein the ratio is one of 0.772 for a six-tooth analysis and 0.913 for a twelve-tooth analysis.

37. A computerized method for determining an anatomical correction for at least one of a maxillary arch and a mandibular arch, comprising the steps of:

measuring with a caliper a plurality of tooth sizes;

receiving by the processor from the caliper a mesiodistal width of a plurality of teeth; and determining the anatomical correction for the at least one of the maxillary arch and the mandibular arch as a function of the mesiodistal width; and displaying the determined anatomical correction.

* * * * *